(12) United States Patent
Fei et al.

(10) Patent No.: US 12,110,416 B1
(45) Date of Patent: Oct. 8, 2024

(54) TEXTILE COATING COMPOSITION THAT REDUCES AND/OR PREVENTS MICROBIAL GROWTH AND/OR CONTROL ODOR(S) FOR PROLONGED TIME PERIODS

(71) Applicant: MICROBAN PRODUCTS COMPANY, Huntersville, NC (US)

(72) Inventors: Xiuzhu Fei, Charlotte, NC (US); Yihong Li, Huntersville, NC (US)

(73) Assignee: MICROBAN PRODUCTS COMPANY, Huntersville, NC (US)

( * ) Notice: Subject to any disclaimer, the term of this patent is extended or adjusted under 35 U.S.C. 154(b) by 0 days.

(21) Appl. No.: 18/618,136

(22) Filed: Mar. 27, 2024

Related U.S. Application Data

(60) Provisional application No. 63/455,048, filed on Mar. 28, 2023.

(51) Int. Cl.
| | |
|---|---|
| *C09D 5/14* | (2006.01) |
| *A01N 37/10* | (2006.01) |
| *A01P 1/00* | (2006.01) |
| *A61L 2/232* | (2006.01) |
| *A61L 101/36* | (2006.01) |
| *C09D 7/63* | (2018.01) |
| *D06M 13/00* | (2006.01) |
| *D06M 13/184* | (2006.01) |
| *D06M 16/00* | (2006.01) |
| *D06M 101/32* | (2006.01) |

(52) U.S. Cl.
CPC .............. *C09D 5/14* (2013.01); *A01N 37/10* (2013.01); *A01P 1/00* (2021.08); *A61L 2/232* (2013.01); *C09D 7/63* (2018.01); *D06M 13/005* (2013.01); *D06M 13/1845* (2013.01); *D06M 16/00* (2013.01); *A61L 2101/36* (2020.08); *A61L 2202/26* (2013.01); *D06M 2101/32* (2013.01)

(58) Field of Classification Search
None
See application file for complete search history.

(56) References Cited

U.S. PATENT DOCUMENTS

| | | |
|---|---|---|
| 2003/0049290 A1 | 3/2003 | Jha et al. |
| 2007/0048344 A1 | 3/2007 | Yahiaoui et al. |
| 2007/0280900 A1 * | 12/2007 | Fox .................. A01N 31/02 424/78.37 |
| 2007/0281999 A1 | 12/2007 | Fox et al. |
| 2009/0074971 A1 | 3/2009 | McMahon et al. |
| 2010/0239679 A1 | 9/2010 | Greene et al. |
| 2019/0276680 A1 | 9/2019 | Baricos et al. |

OTHER PUBLICATIONS

International Search Report and Written Opinion for corresponding PCT Application PCT/US2024/21605; issued Jul. 30, 2024 (20 Pages).

* cited by examiner

*Primary Examiner* — Shawn Mckinnon
(74) *Attorney, Agent, or Firm* — Shumaker, Loop & Kendrick, LLP

(57) ABSTRACT

Antimicrobial and/or anti-odor textile coating composition that reduce and/or prevent bacterial growth and/or control odor(s) on a textile material treated for a prolonged time period including up to, for example, fifty wash cycles. The textile coating compositions may include benzoic acid and at least one of terephthalic acid, and/or a quat silane.

22 Claims, No Drawings

TEXTILE COATING COMPOSITION THAT REDUCES AND/OR PREVENTS MICROBIAL GROWTH AND/OR CONTROL ODOR(S) FOR PROLONGED TIME PERIODS

TECHNICAL FIELD

The present invention relates generally to the field of odor control compositions and textiles treated with the same and more particularly odor control compositions that include benzoic acid and show durable antimicrobial and odor control properties.

BACKGROUND

The current standard in textile antimicrobial and/or odor reduction on textile materials includes the use of heavy metals and/or nanomaterials to reduce specific odors. Formulations with heavy metals and/or nanomaterials can be environmentally harmful as they wash out of textiles and leach into the soil and into ground water. Therefore, safer compounds with potent antimicrobial and odor control properties are preferred.

SUMMARY

Accordingly, there is a need to provide effective and environmentally friendly formulations for antimicrobial and/or odor control that avoid the use of heavy metals and nanomaterials. The compositions, articles, and methods described herein overcome the above-mentioned environmental issues while maintaining effective and durable antimicrobial and/or odor control properties along with improved thermal stability and wash durability. The compositions, articles, and methods described herein utilize benzoic acid to reduce bacterial growth and reduce odor.

In one aspect, a first antimicrobial and/or anti-odor textile coating composition is disclosed, the composition comprising: (a) benzoic acid, and (b) terephthalic acid, wherein the ratio of the benzoic acid to terephthalic acid in the composition is from 2:1 to 8:1. The first antimicrobial and/or anti-odor textile coating composition utilizes terephthalic acid as a cross-linker anchoring benzoic acid to the textile material, such as polyester, via chemical bonding thereby increasing the thermal stability of benzoic acid.

In certain aspects, the first antimicrobial and/or anti-odor textile coating composition is solid at ambient temperatures. In certain aspects, the first antimicrobial and/or anti-odor textile coating composition comprises the benzoic acid at a concentration from 65 weight % to 90 weight % of the total weight of the composition. In certain aspects, the first antimicrobial and/or anti-odor textile coating composition comprises benzoic acid at a concentration from 75 weight % to 85 weight % of the total weight of the composition. In certain aspects, the first antimicrobial and/or anti-odor textile coating composition comprises terephthalic acid at a concentration from 10 weight % to 35 weight % of the total weight of the composition. In certain aspects, the first antimicrobial and/or anti-odor textile coating composition comprises terephthalic acid at a concentration from 15 weight % to 20 weight % of the total weight of the composition.

In certain aspects, the first antimicrobial and/or anti-odor textile coating composition is a liquid, or liquid dispersion, at ambient temperatures. In certain aspects, the antimicrobial and/or anti-odor textile coating composition comprises water from 90 weight % to 98 weight % based on the total weight of the composition. In some aspects, the first antimicrobial and/or anti-odor textile coating composition comprises a dispersant from 0.1 weight % o 2 weight % to aid in dispersing the textile coating composition. In certain aspects, the first antimicrobial and/or anti-odor textile coating composition comprises the benzoic acid at a concentration from 1.3 weight % to 9 weight % of the total weight of the composition. In certain aspects, the first antimicrobial and/or anti-odor textile coating composition comprises the benzoic acid at a concentration from 1.5 weight % to 8.5 weight % of the total weight of the composition. In certain aspects, the first antimicrobial and/or anti-odor textile coating composition comprises the terephthalic acid at a concentration from 0.2 weight % to 3.5 weight % of the total weight of the composition. In certain aspects, the first antimicrobial and/or anti-odor textile coating composition comprises the terephthalic acid at a concentration from 0.3 weight % to 2.0 weight % of the total weight of the composition.

In one aspect, disclosed is a textile material having the first antimicrobial and/or anti-odor textile coating composition described above applied thereon, wherein the textile material reduces bacterial growth, in both gram positive and gram negative bacteria, by a 3 log reduction or greater. In certain aspects, the textile material reduces bacterial growth by a 3 log reduction or greater after twenty-five home launderings.

In certain aspects, the terephthalic acid is directly bound to the textile material and benzoic acid is directly bound to the terephthalic acid such that the benzoic acid forms an outermost surface/layer and terephthalic acid forms an intermediate layer positioned between the textile material and the benzoic acid in the textile material having the antimicrobial and/or anti-odor textile coating composition applied thereon. In certain aspects, the terephthalic acid is covalently bound to the textile material. In certain aspects, the benzoic acid is covalently bound to the terephthalic acid. In certain aspects, the textile material comprises polyester. In certain aspects, the textile material is a polyester-rich material In certain aspects, the composition is present on the textile material from 2 weight % to 10 weight % o.w.f. In certain aspects, the textile material comprises benzoic acid from 1.3 weight % to 9 weight % o.w.f. In certain aspects, the textile material comprises benzoic acid from 1.5 weight % to 8.5 weight % o.w.f. In certain aspects, the textile material comprises terephthalic acid from 0.2 weight % to 3.5 weight % o.w.f. In certain aspects, the textile material comprises terephthalic acid from 0.3 weight % to 2 weight % o.w.f.

In one aspect, disclosed is a method of reducing bacterial growth and odor on a textile, the method comprising: (a) applying the antimicrobial and/or anti-odor textile coating composition disclosed above to a textile material, wherein, applying the antimicrobial and/or anti-odor, textile coating composition comprises padding or exhaustion of the composition onto the textile material to obtain a treated textile material that resists the growth of microbes and controls odor on the textile for a prolonged period of time. In certain aspects, after step (a) the antimicrobial and/or anti-odor textile coating composition is permanently bound to the textile material. In certain aspects, the method further comprises, prior to step (a) preparing and/or providing the antimicrobial and/or anti-odor textile coating composition disclosed above. In certain aspects, this preparing and/or providing step may include mixing the antimicrobial and/or anti-odor textile coating composition with water to form an application bath (liquor bath). In certain aspects, either before or during step (a) a dispersant is added to the application bath to aid in solubilizing the antimicrobial and/or anti-odor textile coating composition and to further aid in application of the composition to the textile material. In certain aspects, the application bath is heated to aid in solubilizing and homogeneously dispersing the antimicrobial and/or anti-odor textile coating composition in the application bath (liquor bath) to aid in a uniform and/or homogeneous application of the composition onto the textile material. In certain aspects, the textile material comprises polyester. In certain aspects, the textile material is a polyester-rich material In certain aspects, the antimicrobial and/or anti-odor textile coating composition is applied to the textile from 2 weight % to 10 weight % o.w.f. In certain aspects, the treated textile material comprises benzoic acid from 1.3 weight % to 9 weight % o.w.f. In certain aspects, the treated textile material comprises benzoic acid from 1.5 weight % to 8.5 weight % o.w.f. In certain aspects, the treated textile material comprises terephthalic acid from 0.2 weight % to 3.5 weight % o.w.f. In certain aspects, the treated textile material comprises terephthalic acid from 0.3 weight % to 2 weight % o.w.f.

In certain aspects, the method reduces bacterial growth on the treated textile material by a 3 log reduction or greater, compared to untreated textile material. In certain aspects, the method reduces bacterial growth on the treated textile material by a 3 log reduction or greater after twenty-five home launderings. In certain aspects, the method reduces bacterial growth on the treated textile material by a 3 log reduction or greater after fifty home launderings.

In one aspect, disclosed is a second antimicrobial and/or anti-odor textile coating composition comprising: (a) benzoic acid and (b) quat silane, wherein the benzoic acid and the quat silane are present in a ratio from 1:4 to 1:2.6. This composition utilizes quat silane to solubilize the benzoic acid. Quat silane can be cured at higher temperatures and forms a coating on the surface of a textile which capture benzoic acid underneath and prevents benzoic acid sublimation and imparts prolonged antimicrobial and/or anti-odor properties.

In certain aspects, the quat silane comprises: 3-(trimethoxysilyl) propyldimethyl octadecyl ammonium chloride, chloropropyltrimethoxysilane, methanol, octadecyldimethylamine, or a combination thereof.

In certain aspects, the benzoic acid is present in the second antimicrobial and/or anti-odor textile coating composition from 20 weight % to 30 weight % of the total weight of the composition. In certain aspects, the benzoic acid is present in the second antimicrobial and/or anti-odor textile coating composition from 23 weight % to 28 weight % of the total weight of the composition. In certain aspects, the quat silane is present in the second antimicrobial and/or anti-odor textile coating composition from 70 weight % to 80 weight % of the total weight of the composition. In certain aspects, the quat silane is present in the second antimicrobial and/or anti-odor textile coating composition from 73 weight % to 78 weight % of the total weight of the composition.

In certain aspects, the second antimicrobial and/or anti-odor textile coating composition comprises water from 80 weight % to 95 weight %. In certain aspects, the benzoic acid is present in the second antimicrobial and/or anti-odor textile coating composition from 1 weight % to 6 weight % of the total weight of the composition. In certain aspects, the benzoic acid is present in the second antimicrobial and/or anti-odor textile coating composition from 1.2 weight % to 5.6 weight % of the total weight of the composition. In certain aspects, the quat silane is present in the second antimicrobial and/or anti-odor textile coating composition from 3.5 weight % to 16 weight % of the total weight of the composition. In certain aspects, the quat silane is present in the second antimicrobial and/or anti-odor textile coating composition from 3.7 weight % to 15.6 weight % of the total weight of the composition.

In one aspect, disclosed is a textile material having the second antimicrobial and/or anti-odor textile coating composition described above applied thereon. In certain aspects, the textile material reduces bacterial growth by a 4 log reduction or greater. In certain aspects, the textile material reduces bacterial growth by a 4 log reduction or greater after twenty-five home launderings. In certain aspects, the textile material reduces bacterial growth by a 4 log reduction or greater after fifty home launderings.

In certain aspects, the textile material comprises polyester. In certain aspects, the textile material is a polyester-rich material.

In certain aspects, the second antimicrobial and/or anti-odor textile coating composition is applied on the textile material from 5 weight % to 20 weight % o.w.f. In certain aspects, the textile material comprises benzoic acid from 1 weight % to 6 weight % o.w.f. In certain aspects, the textile material comprises benzoic acid from 1.2 weight % to 5.6 weight % o.w.f. In certain aspects, the textile material comprises quat silane from 3.5 weight % to 16 weight % o.w.f. In certain aspects, the textile material comprises quat silane from 3.7 weight % to 15.6 weight % o.w.f.

In one aspect, disclosed is a method of reducing bacterial growth and odor on a textile material, the method comprising: (a) applying the second antimicrobial and/or anti-odor textile coating composition described above to a textile material, wherein, applying the antimicrobial and/or anti-odor, textile coating composition comprises padding or exhaustion of the composition onto the textile material to obtain a treated textile material that resists the growth of microbes and controls odor on the textile for a prolonged period of time.

In certain aspects, the second antimicrobial and/or anti-odor textile coating composition is applied on the textile material from 5 weight % to 20 weight % o.w.f. In certain aspects, the treated textile material comprises benzoic acid from 1 weight % to 6 weight % o.w.f. In certain aspects, the treated textile material comprises benzoic acid from 1.2 weight % to 5.6 weight % o.w.f. In certain aspects, the treated textile material comprises quat silane from 3.5 weight % to 16 weight % o.w.f. In certain aspects, the treated textile material comprises quat silane from 3.7 weight % to 15.6 weight % o.w.f. In certain aspects, the textile material comprises polyester. In certain aspects, the textile material is a polyester-rich material. A polyester-rich material, as used herein, refers to any material comprising 50% or greater polyester.

In certain aspects, the method reduces bacterial growth by a 4 log reduction or greater. In certain aspects, the method reduces bacterial growth by a 4 log reduction or greater after twenty-five home launderings. In certain aspects, the method reduces bacterial growth by a 4 log reduction or greater after fifty home launderings.

Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

DETAILED DESCRIPTION

The present invention will now be described more fully hereinafter with reference to the working examples in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

Further, the term "or" as used in this disclosure and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in," "at," and/or "on," unless the context clearly indicates otherwise. The phrase "in one embodiment," as used herein does not necessarily refer to the same embodiment, although it may.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

"Owf" or percent on weight of fabric is generally used in the field and batch processes, the amount of chemical finish to be applied is usually expressed as a weight percentage based on the original fabric weight. This relationship is abbreviated as % owf (percent on weight of fabric), in padding application which is % OWF=[(Weight of Chemical/Weight of Fabric)*100]/Wet pickup rate %; and in exhaustion application which is % OWF=(Weight of Chemical/Weight of Fabric)*100 For example, in padding if a chemical is to be applied at 3% owf to 400 kg of fabric, having a wet pickup rate=80%, then 15 kg of the chemical will be applied onto the fabric (3% of 400 kg at 80% pickup); in exhaustion if a chemical is to be applied at 3% owf to 400 kg of fabric, then 12 kg of the chemical will be applied.

The term "quat silane," "quaternary silane," or "quaternary ammonium silane," as used herein, refers to a class of antimicrobial compounds having a silane, a quaternary ammonium, and a carbon chain, comprising at least eight carbons or greater.

A "coating" as used herein refers to a composition that alters the surface of an article or imparts a property to the surface of the article. A coating may be covalently bound to the surface of the article. Additionally, or alternatively, the coating may be bound to the surface and/or within the surface of the article via electrostatic forces or Van der Waals forces.

Antimicrobial and Odor Control Textile Coating Compositions

Disclosed herein are antimicrobial and odor control textile coating compositions that are configured for application to a textile material to impart antimicrobial and/or odor control properties for a prolonged period of time (e.g. twenty-five wash cycles, fifty wash cycles, several months, or up to a year). The disclosed antimicrobial and odor control compositions are environmentally friendly and are just as effective, in some cases even more effective, than the currently used heavy metal and nanomaterial formulations.

The antimicrobial and odor control textile coating compositions disclosed herein utilize benzoic acid as the main antimicrobial and odor control component. The compositions described herein show improved thermal stability and durable antimicrobial and odor control properties when applied on textiles using the heat-setting and curing methods at high temperatures as compared to untreated textile (textile material without any composition applied thereon).

Benzoic acid is generally difficult to formulate and/or apply on textiles/textile materials due to sublimation and mild degradation of benzoic acid at the high temperatures while heat-setting to and/or on textiles/textile materials. Therefore, when applied on and/or to textiles/textile materials by padding and exhaustion methods, the final heat-setting/curing temperature should not exceed 130° C. However, the typical heat-setting temperature for polyester is from 130° C. to 170° C. Therefore, the low temperature curing limits the use of benzoic acid on textile materials such as polyester. Therefore, in order to utilize benzoic acid in a textile coating composition, a lower temperature must be used and/or an additional component to prevent sublimation or degradation of the benzoic acid.

A first antimicrobial and/or anti-odor textile coating composition utilizes benzoic acid as the main antimicrobial and odor control component along with terephthalic acid as a crosslinker. This composition prevents sublimation and/or degradation of benzoic acid by allowing for the formation of a permanent bond between the textile and benzoic acid via a terephthalic acid anchor. Terephthalic acid bonds the benzoic acid to the textile fibers through cross-linking, or covalent bonding, thereby increasing the thermal stability of benzoic acid as well as improving the performance and wash durability.

The first antimicrobial and/or anti-odor textile coating composition may be a solid composition at ambient temperatures, as benzoic acid has little water solubility and terephthalic acid is insoluble in water. In a water-based application process, the first antimicrobial and odor control composition may require heat and/or an added dispersant to facilitate application onto a textile material. Dispersants include, but are not limited to: fatty amines, alkylnapthalene sulfonate, and more preferably ethoxylated alcohols. Ethoxylated alcohols are preferred due to their stability in the acidic conditions of the first antimicrobial and/or anti-odor textile coating composition. In certain aspects, the dispersant is present at 0.1 weight % to 2 weight % based on the total weight of the composition.

The first textile coating composition may have an operable ratio of benzoic acid to terephthalic acid from 2:1 to 8:1 by weight in which any end point falling therein may serve as an endpoint for additional ranges; additional ranges include more preferably 3:1 to 7:1 and most preferably 4:1 to 6:1. Outside of this ratio antimicrobial and odor control efficacy may still be observed if appropriately applied; however there may be reduced thermal stability and/or reduced wash durability. Additionally, if the amount of benzoic acid is reduced, the composition will have reduced antimicrobial efficacy.

The first antimicrobial and/or anti-odor textile coating composition may be a solid at ambient temperature. Within the solid first antimicrobial and/or anti-odor textile coating composition, benzoic acid may be present in the first antimicrobial and/or anti-odor textile coating composition from 65 weight % to 90 weight % of the composition in which any endpoint falling therein may serve as an endpoint for additional ranges; additional ranges may include, for example, from 70 weight % to 85 weight %, from 75 weight % to 85 weight %, and from 75 weight % to 80 weight %. In certain aspects, the benzoic acid is a benzoate salt, such as sodium benzoate.

Within the solid first antimicrobial and/or anti-odor textile coating composition, terephthalic acid may be present in the first antimicrobial and/or anti-odor textile coating composition from 10 weight % to 35 weight % of the total weight of the composition in which any end point falling therein may serve as an endpoint for additional ranges; additional ranges may include, for example, from 15 weight % to 20 weight %, from 15 weight % to 30 weight %, and from 20 weight % to 25 weight %.

The first antimicrobial and/or anti-odor textile coating composition may be a liquid, or liquid dispersion, at ambient temperatures. The first antimicrobial and/or anti-odor textile coating composition may comprise water from 90 weight % to 98 weight %. The first antimicrobial and/or anti-odor textile coating composition may also comprise a dispersant from 0.1 weight % to 2 weight % to aid in solubilizing the benzoic acid and/or terephthalic acid. The benzoic acid may be present in the first antimicrobial and/or anti-odor textile coating composition from 1.3 weight % to 9 weight % of the composition in which any endpoint falling therein may serve as an endpoint for additional ranges; additional ranges may include, for example, from 1.5 weight % to 8.5 weight %, from 2 weight % to 7 weight %, and from 3 weight % to 5 weight %. In certain aspects, the benzoic acid is a benzoate salt, such as sodium benzoate. Terephthalic acid may be present in the first antimicrobial and/or anti-odor textile coating composition from 0.2 weight % to 3.5 weight % of the total weight of the composition in which any end point falling therein may serve as an endpoint for additional ranges; additional ranges may include, for example, from 0.3 weight % to 2 weight %, from 0.5 weight % to 1.5 weight %, and from 0.75 weight % to 1.3 weight %.

A second antimicrobial and/or anti-odor textile coating composition also utilizes benzoic acid as the main antimicrobial and odor control component along with Quat silane. Quat silane is also known to have antimicrobial properties, however in the present instance it is used as a solubilizing and stabilizing agent to keep benzoic acid in solution and thus mill friendly. In addition to antimicrobial and odor control properties, the second antimicrobial and/or anti-odor textile coating composition imparts water repellency to the treated textile article. Organic solvents, such as methanol, isopropyl alcohol, and acetone are also able to dissolve benzoic acid. However, when it comes to the water-based textile wet process, the benzoic acid recrystallizes and becomes solid again, which makes the treatment on textiles uneven. Therefore, organic solvent alone is not sufficient to stabilize benzoic acid. The second antimicrobial and/or anti-odor textile coating composition prevents sublimation and/or degradation of benzoic acid by forming a layer, or coating, on the surface, which is covalently bound to the polyester surface, encapsulating the benzoic acid within the coating.

The second antimicrobial and/or anti-odor textile coating composition may have benzoic acid to Quat silane at a ratio from 2:5 to 1:4 by weight, wherein any endpoint falling therein may serve as an endpoint for additional ranges. Outside of this ratio antimicrobial and odor control efficacy may still be observed if appropriately applied; however there may be reduced thermal stability, reduced solubility, and/or reduced wash durability.

Within the second antimicrobial and/or anti-odor textile coating composition, benzoic acid may be present in the second antimicrobial and/or anti-odor textile coating composition from 20 weight % to 30 weight % of the total weight of the composition, wherein any endpoint falling therein may serve as an endpoint for additional ranges; additional ranges include 22 weight % to 26 weight %, 23 weight % to 28 weight %, 24 weight % to 26 weight %, 22 weight % to 24 weight %, and 23 weight % to 25 weight %. In certain aspects, the benzoic acid is a benzoate salt, such as sodium benzoate.

Within the second antimicrobial and/or anti-odor textile coating composition, quat silane may be present from 70 weight % to 80 weight % of the total weight of the composition, wherein any endpoint falling therein may serve as an endpoint for additional ranges; additional ranges include: 73 weight % to 78 weight %, 75 weight % to 80 weight %, 75 weight % to 78 weight %, and 72 weight % to 78 weight %. Quat silane may be 3-(trimethoxysilyl) propyldimethyl octadecyl ammonium chloride, chloropropyltrimethoxysilane, methanol, octadecyldimethylamine, or a combination thereof. In certain aspects, Quat silane is a mixture of 3-(trimethoxysilyl) propyldimethyl octadecyl ammonium chloride, chloropropyltrimethoxysilane, methanol, and octadecyldimethylamine. In certain aspects, the Quat Silane comprises 74.9 weight % to 69.1 weight % of 3-(trimethoxysilyl) propyldimethyl octadecyl ammonium chloride, 16% of chloropropyltrimethoxysilane, 10 weight % to 19.5 weight % methanol, and 2 weight % octadecyldimethylamine. While Quat silane is also considered an antimicrobial, benzoic acid is the main antimicrobial and odor control component in the composition.

The second antimicrobial and/or anti-odor textile coating composition may comprise water from 80 weight % to 95 weight %. The benzoic acid may be present in the second antimicrobial and/or anti-odor textile coating composition from 1 weight % to 6 weight % of the composition in which any endpoint falling therein may serve as an endpoint for additional ranges; additional ranges may include, for example, from 1.2 weight % to 5.6 weight %, from 1.5 weight % to 5 weight %, and from 2 weight % to 4 weight %. In certain aspects, the benzoic acid is a benzoate salt, such as sodium benzoate. Quat silane may be present in the second antimicrobial and/or anti-odor textile coating composition from 3.5 weight % to 16 weight % of the total weight of the composition in which any end point falling therein may serve as an endpoint for additional ranges; additional ranges may include, for example, from 3.7 weight % to 5.6 weight %, from 4 weight % to 14 weight %, and from 4.3 weight % to 13 weight %.

Method of Applying the Antimicrobial and Odor Control Compositions

As further discussed and shown in the Working Examples, the antimicrobial and/or anti-odor textile coating compositions may be applied (permanently applied) to a desired textile material during an application process. The antimicrobial and/or anti-odor textile coating compositions may be applied to a desired textile using an exhaustion method. Additionally, or alternatively, the antimicrobial and/or anti-odor textile coating compositions may be applied to a desired textile using a padding method. The application methods described herein result in a uniform, or even, coating of the composition on the textile which results in the textile having no discoloration or surface texture post-application as well as consistent antimicrobial and anti-odor properties on the textile.

For example, for the first antimicrobial and/or anti-odor textile coating composition, when using the padding method, the pad bath is made by combining the first antimicrobial and odor control composition and water, which is approximately 2-10% of the first antimicrobial and/or anti-odor textile coating composition and water. In certain aspects, heat is used to get the first antimicrobial and/or anti-odor textile coating composition into the solution. Additionally, or alternatively, a dispersant may be used to help solubilize the first antimicrobial and/or anti-odor textile coating composition. The dispersant may be added to the composition at the time of formulation. Alternatively, the dispersant may be used during application. The dispersant may be added at a concentration of 0.1 weight % to 2 weight % based on the total weight of the composition. The pad bath is padded onto the desired textile material and is subsequently cured/dried at a temperature from 110° C. to 170° C. in a tenter frame or a drier for a minimum of 45 seconds and up to 5 minutes to obtain a dry textile material that resists the growth of microbes and controls odor on the textile material for a prolonged period of time (e.g., 25 wash cycles, 50 wash cycles, several months, or up to a year).

For example, for the first antimicrobial and/or anti-odor textile coating composition when using the exhausting method, the exhaustion bath is made by combining the first antimicrobial and/or anti-odor textile coating composition and water, which is approximately 2-10% concentrate and water. In certain aspects, heat is used to get the first antimicrobial and/or anti-odor textile coating composition into the solution. Additionally, or alternatively, a dispersant may be used to help solubilize the first antimicrobial and/or anti-odor textile coating composition. The exhaustion may be performed in a beaker dyeing machine that includes the desired textile material, e.g., Lobomat BFA-24 Werner Mathis AG. The exhaustion conditions may include the following: liquor ratio (the ratio of application bath to textile material) of 10 to 1, exhaustion temperature at a temperature from 110° C. to 140° C., dwell time at the exhaustion temperature is from 20 minutes to 50 minutes. This is followed by cooling the textile and liquid media to a temperature from 40° C. to 70° C. After the exhaustion, the treated textile materials were rinsed and then dried in a dyer, optionally in an IR dryer, at a temperature from room temperature (about 20° C.) to 190° C. for at least 45 seconds and up to overnight to obtain a dry textile material that resists the growth of microbes and controls odor on the textile material for a prolonged period of time (e.g., 25 wash cycles, 50 wash cycles, several months, or up to a year).

The first antimicrobial and/or anti-odor textile coating composition, once applied to the textile, results in an antimicrobial and anti-odor textile material wherein benzoic acid forms the outermost surface of the antimicrobial and anti-odor textile material, terephthalic acid forms an intermediate layer between benzoic acid and the surface of the textile material. The application method results in a covalent bond between terephthalic acid and the textile chain as well as a covalent bond between terephthalic acid and benzoic acid.

For example, for the second antimicrobial and/or anti-odor textile coating composition when using the padding method, the pad bath is made by combining the second textile coating composition and water. The pad bath comprises approximately 5-20% of the second antimicrobial and/or anti-odor textile coating composition. The pad bath is padded onto the desired textile material and is subsequently cured/dried at a temperature from 110° C. to 170° C. in a tenter frame or a drier for a minimum of 45 seconds and up to 5 minutes to obtain a dry textile material that resists the growth of microbes and controls odor on the textile material for a prolonged period of time (e.g., 25 wash cycles, 50 wash cycles, several months, or up to a year).

For example, for the second antimicrobial and/or anti-odor textile coating composition when using the exhausting method, the exhaustion bath is made by combining the second antimicrobial and/or anti-odor textile coating composition and water. The exhaustion bath comprises approximately 5-20% of the second textile coating composition. The exhaustion may be performed in a beaker dyeing machine that includes the desired textile material, e.g., Lobomat BFA-24 Werner Mathis AG. The exhaustion conditions may include the following: liquor ratio (the ratio of application bath to textile material) of 10 to 1, exhaustion temperature at a temperature from 110° C. to 140° C., dwell time at the exhaustion temperature is from 20 minutes to 50 minutes. This is followed by cooling the textile and liquid media to a temperature from 40° C. to 70° C. After the exhaustion, the treated textile materials were rinsed and then dried in a dyer, optionally in an IR dryer, at a temperature from room temperature (about 20° C.) to 190° C. for at least 45 seconds and up to overnight to obtain a dry textile material that resists the growth of microbes and controls odor on the textile material for a prolonged period of time (e.g., 25 wash cycles, 50 wash cycles, several months, or up to a year).

Textile Materials Having the Antimicrobial and Odor Control Formulations

Further disclosed herein are textile materials having one of the above-mentioned antimicrobial and/or anti-odor textile coating compositions applied thereon. The textile material having either the first antimicrobial and/or anti-odor textile coating composition or the second antimicrobial and/or anti-odor textile coating composition applied thereon will prevent antimicrobial growth as well as prevent any odors caused by microbes for a prolonged period of time in comparison to textile material not treated with the antimicrobial and odor control compositions.

In certain aspects, the textile material includes the first antimicrobial and/or anti-odor textile coating composition applied thereon. In this aspect, the first antimicrobial and/or anti-odor textile coating composition is applied at a concentration ranging from 2% weight on fabric (owf) to 10% owf, more preferably 4% owf to 8% owf, and most preferably 5% owf to 7% owf. In this aspect, the dry textile material treated with the first antimicrobial and/or anti-odor textile coating composition will have benzoic acid applied thereon at a concentration ranging from 1.3% owf to 9.0% owf, more preferably 1.8% owf to 6.7% owf, and most preferably 4.5% owf to 5.2% owf; and terephthalic acid applied thereon at a concentration ranging from 0.2% owf to 3.5% owf, from 0.3% owf to 2.0% owf, more preferably 0.7% owf to 1.2% owf, and most preferably 0.7% owf to 1.1% owf.

In certain aspects, the dry textile material includes the second antimicrobial and/or anti-odor textile coating composition applied thereon. In this aspect, the second antimicrobial and/or anti-odor textile coating composition is applied at a concentration ranging from 5% owf to 20% owf, more preferably 7% owf to 15% owf, and most preferably 8% owf to 10% owf. In this aspect, the dry textile material treated with the second antimicrobial and/or anti-odor textile coating composition will have benzoic acid applied thereon at a concentration ranging from 1% owf to 6% owf, from 1.2% owf to 5.6% owf, more preferably 1.4% owf to 4% owf, and most preferably 2.0% owf to 2.5% owf; and quat silane applied thereon at a concentration ranging from 3.5% owf to 16% owf, 3.7% owf to 15.6% owf, more preferably 4% owf to 14.4% owf, and most preferably 6% owf to 8% owf.

In view of the above mentioned concentrations and ratios, the textile material and/or the composition applied thereon reduces microbial growth for prolonged periods of time by a 3 log reduction or greater, more preferably by a 3.5 log reduction or greater, and most preferably by a 4.0 log reduction or greater.

In certain preferred aspects, the textile materials disclosed herein, including the textile materials, are either woven or non-woven textile materials. In certain preferred embodiments, the textile materials and/or textile materials are knitted/woven fabrics, including, polyester, nylon, rayon, cotton, or any combination thereof. In certain aspects, the textile material/dry textile material includes a fabric weight ranging from 20-400 gsm (grams per square meter). It should be further appreciated that heavier weighted fabrics will absorb more of the above disclosed compositions (e.g., during and post-padding and/or during and post-exhaustion) resulting in a textile material having better odor control/capture for prolonged periods of time.

WORKING EXAMPLES

As a first comparative example, benzoic acid was applied via exhaustion at 6% owf to polyester and cured at 170° C. The Antimicrobial Textile Test AATCC TM 100 was performed to determine the log reduction of *Klebsiella pneumonia* both prior to laundering and after twenty-five home launderings. The data from AATCC TM 100 is shown in Table 1 below. Benzoic acid shows little to no antimicrobial properties prior to laundering and no antimicrobial properties after washing. This is due to benzoic acids thermal instability.

TABLE 1

|  | AATCC TM 100 (0 HL) kP | AATCC TM 100 (25 HL) kP |
|---|---|---|
| Log Reduction | 0.0 | 0.0 |
| Log Reduction | 0.7 | 0.0 |
| Log Reduction | 0.5 | 0.0 |
| Average | 0.4 | 0.0 |
| STDEV | 0.3 | 0 |

A second comparative example was evaluated. The second comparative composition having the quat silane mixture without benzoic acid. The second comparative composition comprises: 72 wt % 3-(trimethoxysilyl) propyldimethyl octadecyl ammonium chloride, 16 wt % chloropropyltrimethoxysilane, and 2 wt % octadecyldimethylamine in methanol. The second comparative composition was applied to polyester via exhaustion at 9% owf and cured at 170° C. The Antimicrobial Textile Test AATCC TM 100 was performed to determine the log reduction of *Klebsiella pneumonia* and *Staphylococcus aureus* both prior to laundering and after twenty-five home launderings. The data from AATCC TM 100 is shown in Table 2 below. When the composition is formulated without benzoic acid there is no log reduction in *Klebsiella pneumonia* growth. Additionally, when the composition is formulated without benzoic acid the composition does not have any wash durability. The log reduction in *Staphylococcus aureus* growth is nearly diminished after twenty-five home launderings.

TABLE 2

|  | AATCC TM 100 (0 HL) kP | AATCC TM 100 (25 HL) kP | AATCC TM 100 (0 HL) Sa | AATCC TM 100 (25 HL) Sa |
|---|---|---|---|---|
| Log Reduction | 0 | 0 | 4.7 | 0.2 |
| Log Reduction | 0 | 0 | 4.7 | 0.3 |
| Log Reduction | 0 | 0 | 4.7 | 0.2 |
| Average | 0 | 0 | 4.7 | 0.2 |
| STDEV | 0 | 0 | 0 | 0.1 |

A first antimicrobial and/or anti-odor textile coating composition was prepared by combining 83.3 wt % benzoic acid and 16.75 wt % terephthalic acid. The first antimicrobial and/or anti-odor textile coating composition was dissolved in water and applied to polyester via exhaustion at 6% owf and cured at 170° C. The Antimicrobial Textile Test AATCC TM 100 was performed to determine the log reduction of *Klebsiella pneumonia* and *Staphylococcus aureus* both prior to laundering and after twenty-five home launderings. The data from AATCC TM 100 is shown in Table 3 below. When benzoic acid is formulated with terephthalic acid the benzoic acid has improved thermal stability and durability as the terephthalic acid bond/cross-links the benzoic acid to the polyester fibers of the textile material.

TABLE 3

|  | AATCC TM 100 (0 HL) kP | AATCC TM 100 (25 HL) kP | AATCC TM 100 (0 HL) Sa | AATCC TM 100 (25 HL) Sa |
|---|---|---|---|---|
| Log Reduction | 3.0 | 4.7 | 4.7 | 4.7 |
| Log Reduction | 3.9 | 4.7 | 4.7 | 4.7 |
| Log Reduction | 3.6 | 4.7 | 3.9 | 4.7 |
| Average | 3.5 | 4.7 | 4.4 | 4.7 |
| STDEV | 0.4 | 0 | 0.2 | 0 |

A second antimicrobial and/or anti-odor textile coating composition was prepared by combining 25 wt % benzoic acid and 75 wt % quat silane (72 wt % 3-(trimethoxysilyl) propyldimethyl octadecyl ammonium chloride, 16 wt % chloropropyltrimethoxysilane, and 2 wt % octadecyldimethylamine in methanol). The second antimicrobial and/or anti-odor textile coating composition was dissolved in water and applied via padding at 9% owf and cured at 170° C. The Antimicrobial Textile Test AATCC TM 100 was performed to determine the log reduction of Klebsiella pneumonia and Staphylococcus aureus both prior to laundering, after twenty-five home launderings, and after fifty home launderings. The data from AATCC TM 100 is shown in Table 4 below. When benzoic acid is formulated with quat silane the textile shows an improved reduction in bacterial growth compared to the comparative example above. Additionally, when formulated with quat silane, the antimicrobial effects are prolonged over twenty-five home launderings and fifty home launderings. Benzoic acid is stabilized by quat silane and, when cured at high temperatures, quat silane forms polymeric structures that capture benzoic acid and prevent sublimation. Quat silane itself is an antimicrobial solution. However, due to the characteristic of quat silane chemistry, it only shows antimicrobial performance when tested against ASTM E2149 test method, using Accelerated Laundry followed by a salt-methanol rinse. In this formula, benzoic acid remains the key antimicrobial ingredient while quat silane is just the solubilizing agent. The performance of treated fabric can be tested against any of the common antimicrobial method, including but not limited to AATCC TM 100, ISO 20743, and JIS L 1902. In addition, it can be washed by the regular home laundry without the salt-methanol rinse. The water repellency of a textile treated with 9% owf of the second antimicrobial composition was determined using AATCC TM 22 and had a score of 75, compared to the untreated textile with a score of 0.

TABLE 4

|  | AATCC TM 100 (0 HL) kP | AATCC TM 100 (25 HL) kP | AATCC TM 100 (50 HL) kP | AATCC TM 100 (0 HL) Sa | AATCC TM 100 (25 HL) Sa |
|---|---|---|---|---|---|
| Log Reduction | 4.7 | 4.7 | 4.7 | 4.7 | 4.7 |
| Log Reduction | 4.7 | 4.7 | 4.7 | 4.7 | 4.7 |
| Log Reduction | 4.7 | 3.3 | 4.7 | 4.7 | 4.7 |
| Average | 4.7 | 4.2 | 4.7 | 4.7 | 4.7 |
| STDEV | 0 | 0.7 | 0 | 0 | 0 |

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. An antimicrobial and/or anti-odor, textile coating composition that reduces and/or prevents microbial growth and/or controls odor(s) on a textile material comprising:
    (a) from 65 weight % to 90 weight % benzoic acid, based on the total weight of the composition; and
    (b) terephthalic acid;
    wherein the benzoic acid and the terephthalic acid are present in the composition at a ratio of 2:1 to 8:1.

2. The antimicrobial and/or anti-odor, textile coating composition according to claim 1, wherein the benzoic acid is present from 75 weight % to 85 weight % of the total weight of the composition.

3. The antimicrobial and/or anti-odor, textile coating composition according to claim 1, wherein the terephthalic acid is present from 10 weight % to 35 weight % of the total weight of the composition.

4. The antimicrobial and/or anti-odor, textile coating composition according to claim 1, wherein the terephthalic acid is present from 15 weight % to 20 weight % of the total weight of the composition.

5. A textile material having the antimicrobial and/or anti-odor, textile coating composition according to claim 1 applied thereon, wherein the textile material reduces bacterial growth by a 3 log reduction or greater when compared with an untreated textile material.

6. The textile material according to claim 5, wherein benzoic acid forms an outermost layer and terephthalic acid forms an intermediary layer positioned between the benzoic acid and the textile material having the textile coating composition applied thereon.

7. The textile material according to claim 5, wherein the textile material reduces bacterial growth by a 3 log reduction or greater after twenty-five home launderings when compared with an untreated textile material.

8. The textile material according to claim 5, wherein the textile material comprises polyester.

9. The textile material according to claim 5, wherein the antimicrobial and/or anti-odor, textile coating composition is present on the textile from 2 weight % to 10 weight % on weight of fabric.

10. The textile material according to claim 5, wherein the textile material comprises benzoic acid from 1.3 weight % to 9 weight % based on weight of fabric.

11. The textile material according to claim 5, wherein the textile material comprises terephthalic acid from 0.2 weight % to 3.5 weight % based on weight of fabric.

12. A method of reducing and/or preventing microbial growth and/or odor on a textile material, the method comprising:
    a. applying the antimicrobial and/or anti-odor, textile coating composition according to claim 1 to a textile material;
    wherein, applying the antimicrobial and/or anti-odor, textile coating composition comprises padding or exhaustion of the composition onto the textile material to obtain a treated textile material that resists the growth of microbes and controls odor on the textile for a prolonged period of time.

13. The method according to claim 12, further comprising, prior to step (a), adding the antimicrobial and/or anti-odor, textile coating composition according to claim 1 to water to create an application bath.

14. The method according to claim 13, further comprising adding a dispersant to the application bath, heating the mixture, or a combination thereof.

15. The method according to claim 12, wherein the antimicrobial and/or anti-odor, textile coating composition is applied to the textile from 2 weight % to 10 weight % on weight of fabric.

16. The method according to claim 12, wherein the benzoic acid is present on the treated textile from 1.3 weight % to 9 weight % on weight of fabric.

17. The method according to claim 12, wherein the benzoic acid is present on the treated textile from 1.5 weight % to 8.5 weight % on weight of fabric.

18. The method according to claim 12, wherein the terephthalic acid is present on the treated textile from 0.2 weight % to 3.5 weight % on weight of fabric.

19. The method according to claim 12, wherein the terephthalic acid is present on the treated textile from 0.3 weight % to 2.0 weight % based on weight of fabric.

20. The method according to claim 12, wherein the method reduces bacterial growth on the treated textile material by a 3 log reduction or greater.

21. The method according to claim 12, wherein the method reduces bacterial growth on the treated textile material by a 3 log reduction or greater after twenty-five home launderings.

22. The method according to claim 12, wherein the textile material comprises polyester.

* * * * *